United States Patent [19]

Jacobsen et al.

[11] Patent Number: 5,532,236
[45] Date of Patent: Jul. 2, 1996

[54] [1,2,4]TRIAZOLO[4,3-A]QUINOXALINE COMPOUNDS

[75] Inventors: Poul Jacobsen, Slangerup; Flemming E. Nielsen; Lone Jeppesen, both of Virum, all of Denmark

[73] Assignee: Novo Nordisk A/S, Bagsvaerd, Denmark

[21] Appl. No.: 237,518

[22] Filed: May 3, 1994

[30] Foreign Application Priority Data

May 6, 1993 [DK] Denmark .................................. 0535/93
Nov. 12, 1993 [DK] Denmark .................................. 1287/93

[51] Int. Cl.$^6$ ...................... C07D 487/14; C07D 417/14; A61K 31/505; A61K 31/54
[52] U.S. Cl. .................... 514/228.5; 514/233.2; 514/250; 544/60; 544/115; 544/346
[58] Field of Search ............................. 514/233.2, 228.5, 514/250; 544/60, 115, 346

[56] References Cited

U.S. PATENT DOCUMENTS 4,400,382  8/1983  Brown et al. ........................... 514/250

FOREIGN PATENT DOCUMENTS

WO93/06103  4/1993  WIPO.

OTHER PUBLICATIONS

Loev et al., J. Med. Chem., 1985, vol. 28, pp. 363–366.
Khandwala et al., Chemical Abstracts, vol. 100, No. 23, entry 100:185, 318, 1984.
Sastry et al, Chemical Abstracts, vol. III, No. 25, entry 611:232, 733, 1989.
Jacobsen et al, Chemical Abstracts, vol. 119, No. 11, entry 119:117, 278, 1993.

Primary Examiner—Mukund J. Shah
Assistant Examiner—Matthew V. Grumbling
Attorney, Agent, or Firm—Steve T. Zelson; Elias J. Lambiris

[57] ABSTRACT

The present invention relates to [1,2,4]triazolo[4,3-a quinoxaline derivatives of formula I

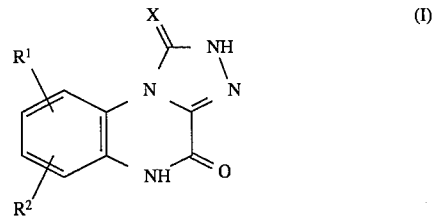

wherein one of $R^1$ and $R^2$ is a 5- or 6-membered nitrogen-containing heterocyclic ring which is optionally substituted with one, two or three substituents, wherein each substituent is independently phenyl or $C_{1-6}$-alkyl, or one of $R^1$ and $R^2$ is a fused ring system comprising a 5- or 6-membered nitrogen-containing heterocyclic ring and a benzene, pyridine, pyrimidine or pyrazine ring, wherein the fused ring system is optionally substituted with phenyl or $C_{1-6}$-alkyl; and the other of $R^1$ and $R^2$ is hydrogen, $C_{1-6}$-alkyl, $C_{1-6}$-alkoxy, halogen, $NO_2$, $NH_2$, CN, $CF_3$, $COC_{1-6}$-alkyl or $SO_2NR'R''$, wherein R' and R'' are independently hydrogen or $C_{1-6}$-alkyl; and X is O or S; and pharmaceutically acceptable salts thereof. The compounds have affinity for the AMPA receptors and are antagonists in connection with this type of receptors which makes them useful in the treatment of CNS ailments, especially in the treatment of any of the numerous indications caused by hyperactivity of excitatory amino acids.

32 Claims, No Drawings

[1,2,4]TRIAZOLO[4,3-A]QUINOXALINE COMPOUNDS

The present invention relates to therapeutically active heterocyclic compounds, a method of preparing the same, pharmaceutical compositions comprising the compounds, and a method of treating therewith.

More specifically, the invention relates to novel [1,2,4]triazolo[4,3-a]quinoxaline derivatives which are useful in the treatment of any indication caused by hyperactivity of excitatory amino acids.

L-glutamic acid, L-aspartic acid and a number of other closely related amino acids have in common the ability to activate neurons in the central nervous system (CNS). Biochemical, electrophysiological and pharmacological studies have substantiated this and demonstrated that acidic amino acids are transmitters for the vast majority of excitatory neurons in the mammalian CNS.

Interaction with glutamic acid mediated neurotransmission is considered a useful approach in the treatment of neurological and psychiatric diseases. Thus, known antagonists of excitatory amino acids have shown potent anxiolytic (Stephens et al., Psychopharmacology 90, 143–147, 1985), anticonvulsant (Croucher et al., Science 216, 899–901, 1982) and muscle relaxant properties (Turski et al., Neurosci. Lett. 53, 321–326, 1985).

It has been suggested that accumulation of extracellular excitatory amino acids, followed by overstimulation of neurons, may explain the neuronal sclerosis, Parkinsonism, Alzheimer's disease, Huntington's disease, epilepsy, and deficiencies of mental and motor performance seen after conditions of brain ischemia, anoxia and hypoglycemia or head and spinal cord trauma (McGeer et al., Nature 263, 517–519, 1976; Simon et al., Science 226, 850–852, 1984; Wieloch, Science 230, 681–683, 1985; Faden et al., Science 244, 798–800, 1989; Turski et al., Nature 349, 414–418, 1991). Other possible indications are psychosis, muscle rigidity, emesis and analgesia.

Excitatory amino acids exert their actions via specific receptors located postsynaptically or presynaptically. Such receptors are at present conveniently subdivided into three groups bases on electrophysiological and neurochemical evidence: 1 the NMDA (N-methyl-D-aspartate) receptors, 2 the AMPA receptors, and 3 the kainate receptors. L-glutamic acid and L-aspartic acid probably activate all the above types of excitatory amino acid receptors and possibly other types as well.

The above mentioned classification of excitatory amino acid receptors into NMDA, AMPA, and kainate receptors is based primarily on the following electrophysiological and neurochemical findings.

1) N-methyl-D-aspartate (NMDA) receptors exhibit high selectivity for the excitant NMDA. Ibotenic acid, L-homocysteic acid, D-glutamic acid and trans-2,3-piperidine dicarboxylic acid (trans-2,3-PDA) exert a strong to moderate agonist activity on these receptors. The most potent and selective antagonists are the D-isomers of the 2-amino-5-phosphonocarboxylic acids, e.g. 2-amino-5-phosphono-valeric acid (D-APV) and 3-[(±)-2-carboxy-piperazin-4-yl]-propyl-1-phosphonic acid (CPP), while moderate antagonist activity is shown by the D-isomers of long chain 2-amino dicarboxylic acids (e.g. D-2-amino-adipic acid) and long chain diaminodicarboxylic acids (e.g. diaminopimelic acid). The NMDA-induced synaptical responses have been extensively investigated in the mammalian CNS, especially in the spinal cord (J. Davies et al., J. Physiol. 297, 621–635, 1979) and the responses have been shown to be strongly inhibited by $Mg^{2+}$.

2) AMPA receptors are activated selectively by AMPA (2-amino-3-hydroxy-5-methyl-4-isoxazolepropionic acid), other potent agonists being quisqualic acid and L-glutamic acid. Glutamic acid diethyl ester (GDEE) is a selective but very weak antagonist of this site. AMPA receptors are relatively insensitive to $Mg^{2+}$.

Glutamate release has long been thought to play a major role in neuronal death resulting from cerebral ischemia (Benveniste, H. et al., J. Neurochem. 43, 1369–1374, 1984). It is well known that NMDA receptor evoked $Ca^{2+}$ influx is an important mechanism in ischemic neuronal cell loss. The non-NMDA receptor coupled ionophor is not permeable to calcium. However, the excitation by the Scaffer collaterals in the CA1 region is excerted by non-NMDA receptors, and this fact is of importance for the events in the postischemic period. Recent studies have shown that selective AMPA antagonists have neuroprotectant effects in global ischemia in the gerbil even when given several hours after reperfusion (Sheardown et al., Science 247, 571–574, 1990).

AMPA antagonists are therefore useful in the treatment of cerebral ischemia.

3) Kainate receptors. Excitatory responses to kainic acid are relatively insensitive to antagonism by NMDA-antagonists and by GDEE, and it has been proposed that kainic acid activates a third subclass of acidic amino acid receptor. Certain lactonized derivatives of kainic acid are selective antagonists (O. Goldberg et al., Neurosci. Lett. 23, 187–191, 1981) and the dipeptide 3-glutamyl-glycine also shows some selectivity for kainate receptors. $Ca^{2+}$ but not $Mg^{2+}$ is a strong inhibitor of kainic acid binding.

Surprisingly, it has now been found that the novel [1,2,4]triazolo[4,3-a]quinoxaline derivatives of the general formula I

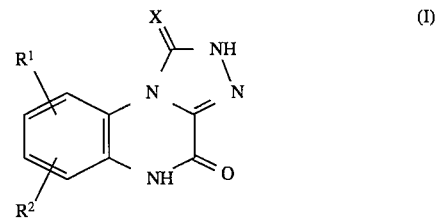

wherein one of $R^1$ and $R^2$ is a 5- or 6-membered nitrogen-containing heterocyclic ring optionally mono-, di- or trisubstituted with one or more of phenyl and $C_{1-6}$-alkyl, or one of $R^1$ and $R^2$ is a fused ring system comprising a 5- or 6-membered nitrogen-containing heterocyclic ring and one or two monocyclic rings, such as benzene, pyridine, pyrimidine or pyrazine optionally substituted with phenyl or $C_{1-6}$-alkyl; and the other of $R^1$ and $R^2$ is hydrogen, $C_{1-6}$-alkyl, $C_{1-6}$-alkoxy, halogen, $NO_2$, $NH_2$, CN, $CF_3$, $COC_{1-6}$-alkyl or $SO_2NR'R''$, wherein R' and R'' are independently hydrogen or $C_{1-6}$-alkyl; and X is O or S; and pharmaceutically acceptable salts thereof, have affinity for the AMPA receptors and are antagonists in connection with this type of receptor which makes them useful in the treatment of any of the numerous indications caused by hyperactivity of excitatory amino acids.

The term "$C_{1-6}$-alkyl" as used herein refers to a straight or branched, saturated hydrocarbon chain having 1–6 carbon atoms such as methyl, ethyl, propyl, isopropyl, 2-butyl, tert.butyl, 3-pentyl, neopentyl or n-hexyl.

The term "$C_{1-6}$-alkoxy" as used herein refers to a monovalent substituent comprising an $C_{1-6}$-alkyl group linked through an ether oxygen having its free valence bond from the ether oxygen, e.g. methoxy, ethoxy, propoxy, butoxy, pentoxy.

The term "5- or 6-membered nitrogen-containing heterocyclic ring" as used herein refers to a monocyclic unsaturated or saturated ring containing one or more nitrogen atoms and having 5 or 6 members, e.g. pyrrolidinyl, pyrrolinyl, imidazolidinyl, pyrazolidinyl, pyrazolinyl, piperidino, piperidyl, piperazinyl, pyrrolyl, 2H-pyrrolyl, imidazolyl, pyrazolyl, triazolyl, pyridyl, pyrazinyl, pyrimidinyl, pyridazinyl, morpholino, thiomorpholino, isothiazolyl, isoxazolyl, oxazolyl, oxadiazolyl, thiadiazolyl, thiazolyl.

The term "fused ring system" as used herein refers to a multiple ring system preferably having 2 or 3 fused rings in a linear or branched arrangement.

Preferred fused ring systems comprising a 5- or 6-membered nitrogen-containing heterocyclic ring are indolinyl, isoindolinyl, benzimidazolyl, indolizinyl, isoindolyl, 3H-indolyl, indolyl, indazolyl, purinyl, 4H-quinolizinyl, isoquinolyl, quinolyl, phthalazinyl, naphthyridinyl, quinoxalinyl, quinazolinyl, cinnolinyl, pteridinyl, carbazolyl, carbolinyl, acridinyl, phenazinyl.

In a preferred embodiment of the invention, one of $R^1$ and $R^2$ is imidazolyl, triazolyl, piperidino, piperazinyl, morpholino, thiomorpholino, benzimidazolyl, imidazolyl substituted with one or more of phenyl and/or $C_{1-6}$-alkyl, preferably methyl, ethyl, propyl or isopropyl; and the other of $R^1$ and $R^2$ is hydrogen, $C_{1-6}$-alkyl, preferably methyl, ethyl, isopropyl, tert.butyl, halogen, preferably Cl or Br, $NO_2$, CN or $CF_3$.

Preferred compounds of the invention are:
7-(1H-Imidazol-1-yl)[1,2,4]triazolo[4,3-a]quinoxaline-1, 4(2H,5H)-dione;
7-(1H-Imidazol-1-yl)-8-trifluoromethyl[1,2,4]triazolo[4,3-a]quinoxaline-1,4(2H,5H)-dione;
8-Bromo-7-(1H-imidazol-1-yl)[1,2,4]triazolo[4,3-a]quinoxaline-1,4(2H,5 H)-dione;
8-(2-Methyl-1H-imidazol-1-yl)-7-trifluoromethyl[1,2,4]triazolo[4,3-a]quinoxaline-1,4(2H,5H)-dione;
8-(4-Methyl-1H-imidazol-1-yl)-7-trifluoromethyl[1,2,4]triazolo[4,3-a]quinoxaline-1,4(2H,5H)-dione;
8-(1H-Imidazol-1-yl)-7-trifluoromethyl[1,2,4]triazolo[4,3-a]quinoxaline-1,4(2H,5H)-dione;
8-Morpholino-7-trifluoromethyl[1,2,4]triazolo[4,3-a]quinoxaline-1,4(2H,5H)-dione;
8-Piperidino-7-trifluoromethyl[1,2,4]triazolo[4,3-a]quinoxaline-1,4(2H,5H)-dione;
8-(4-Methylpiperazin-1-yl)-7-trifluoromethyl[1,2,4]triazolo[4,3-a]quinoxaline-1,4(2H,5H)-dione;
8-(2,4-Dimethyl-1H-imidazol-1-yl)-7-trifluoromethyl[1,2,4]triazolo[4,3-a]quinoxaline-1,4(2H,5H)-dione, hydrochloride;
8-(2,4-Dimethyl-1H-imidazol-1-yl)-7-trifluoromethyl[1,2,4]triazolo[4,3-a]quinoxaline-1,4(2H,5H)-dione;
8-(1H-Imidazol-1-yl)-7-nitro[1,2,4]triazolo[4,3-a]quinoxaline-1,4(2H,5 H)-dione;
7-Nitro-8-thiomorpholino[1,2,4]triazolo[4,3-a]quinoxaline-1,4(2H,5H)-dione;
8-(4-Phenyl-1H-imidazol-1-yl)-7-nitro[1,2,4]triazolo[4,3-a]quinoxaline-1,4 -(2H,5H)-dione;
8-Morpholino-7-nitro[1,2,4]triazolo[4,3-a]quinoxaline-1, 4(2H,5H)-dione;
8-(2-Isopropyl-1H-imidazol-1-yl)-7-nitro[1,2,4]triazolo[4, 3-a]quinoxaline-1,4(2H,5H)-dione;
8-(2-n-Propyl-1H-imidazol-1-yl)-7-nitro[1,2,4]triazolo[4,3-a]quinoxaline-1,4(2H,5H)-dione;
8-(1H-Benzimidazol-1-yl)-7-nitro[1,2,4]triazolo[4,3-a]quinoxalin-1,4(2H,5 H)-dione;
8-(2-Ethyl-4-methyl-1H-imidazol-1-yl)-7-trifluoromethyl [1,2,4]triazolo[4,3 -a]quinoxaline-1,4(2H,5H)-dione, hydrochloride;
8-(2-n-Propyl-1H-imidazol-1-yl)-7-trifluoromethyl[1,2,4]triazolo[4,3-a]quinoxaline-1,4(2H,5H)-dione, hydrochloride;
8-(2-Isopropyl-1H-imidazol-1-yl)-7-trifluoromethyl[1,2,4]triazolo[4,3-a]quinoxaline-1,4(2H,5H)-dione;
8-(4-Methyl-2-phenyl-1H-imidazol-1-yl)-7-trifluoromethyl [1,2,4]triazolo-[4,3-a]quinoxaline-1,4(2H,5H)-dione, hydrochloride;
7-Chloro-8-(2-ethyl-4-methyl-1H-imidazol-1-yl)[1,2,4]triazolo[4,3-a]quinoxaline-1,4(2H,5H)-dione;
7-Cyano-8-(1H-imidazol-1-yl)[1,2,4]triazolo[4,3-a]quinoxaline-1,4(2H,5H)-dione;
7-Cyano-8-(2-ethyl-4-methyl-1H-imidazol-1-yl)[1,2,4]triazolo[4,3-a]quinoxaline-1,4(2H,5H)-dione, hydrochloride;
8-(1H-imidazol-1-yl)-1-thioxo-7-trifluoromethyl[1,2,4]triazolo[4,3-a]quinoxalin-4(5H)-one;

Other preferred compounds of the invention are:
8-(5-Methyl-1H-imidazol-1-yl)-7-trifluoromethyl[1,2,4] triazolo[4,3-a]quinoxaline-1,4(2H,5H)-dione;
8-Chloro-7-(1H-imidazol-1-yl)[1,2,4]triazolo[4,3-a]quinoxalin-1,4(2H,5 H)-dione;
8-Cyano-7-(1H-imidazol-1-yl)[1,2,4]triazolo[4,3-a]quinoxalin-1,4(2H,5H)-dione;
7-(1H-Imidazol-1-yl)-8-nitro[1,2,4]triazolo[4,3-a]quinoxalin-1,4(2H,5H)-dione;
8-(1H-Imidazol-1-yl)-6-nitro[1,2,4]triazolo[4,3-a]quinoxalin-1,4(2H,5H)-dione;
7-Chloro-8-(1H-imidazol-1-yl)[1,2,4]triazolo[4,3-a]quinoxalin-1,4(2H,5 H)-dione;
6-Bromo-8-(1H-imidazol-1-yl)[1,2,4]triazolo[4,3-a]quinoxalin-1,4(2H,5 H)-dione;
8-(1H-Imidazol-1-yl)[1,2,4]triazolo[4,3-a]quinoxalin-1, 4(2H,5H)-dione;
8-(4-Methyl-1H-imidazol-1-yl)-7-trifluoromethyl[1,2,4] triazolo[4,3-a]quinoxalin-1,4(2H,5H)-dione;
8-(4-Phenyl-1H-imidazol-1-yl)-7-trifluoromethyl[1,2,4] triazolo[4,3-a]quinoxalin-1,4(2H,5H)-dione;
8-(1H-Triazol-1-yl)-7-trifluoromethyl[1,2,4]triazolo[4,3-a] quinoxalin-1,4(2H,5H)-dione.

The compounds of the invention may be present in different tautomeric forms. Therefore the invention includes all such tautomeric forms.

Another embodiment of the invention is pharmaceutically acceptable salts of [1,2,4]triazolo[4,3-a]quinoxaline derivatives of formula I. Such salts include those derived from inorganic and organic acids such as hydrochloric acid, hydrobromic acid, sulfuric acid, nitric acid, oxalic acid, fumaric acid, tartaric acid, etc.

The invention also relates to a method of preparing the above mentioned compounds. The present compounds of formula I are prepared by a) substituting a compound having the formula II

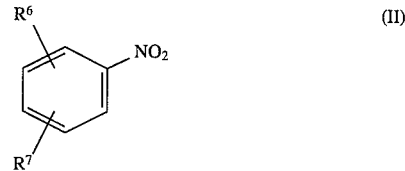

wherein one of $R^6$ and $R^7$ is halogen or $C_{1-6}$-alkoxy; and the other of $R^6$ and $R^7$ is hydrogen, $C_{1-6}$-alkyl, $C_{1-6}$-alkoxy, halogen, $NO_2$, $NH_2$, CN, $CF_3$, $COC_{1-6}$-alkyl or $SO_2NR'R''$, wherein R' and R'' are independently hydrogen or $C_{1-6}$-alkyl, with a 5- or 6-membered nitrogen-containing heterocyclic ring optionally mono-, di- or trisubstituted with one or more of phenyl and $C_{1-6}$-alkyl or with a fused ring system comprising a 5- or 6-membered nitrogen-containing heterocyclic ring optionally substituted with phenyl or $C_{1-6}$-alkyl, to form a compound of the formula III

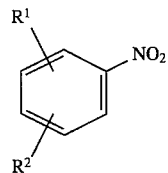

(III)

wherein $R^1$ and $R^2$ have the meanings defined above for formula I and hydrogenating or reducing the compound to form a compound of the formula IV

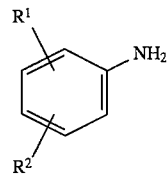

(IV)

wherein $R^1$ and $R^2$ have the meanings defined above, and reacting the compound with an alkyl oxalylhalogenide to form a compound of the formula V

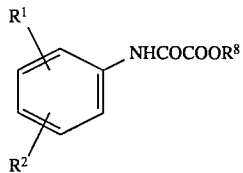

(V)

wherein $R^1$ and $R^2$ have the meanings defined above and $R^8$ is $C_{1-6}$-alkyl, and nitrating the compound to form a compound of the formula VI

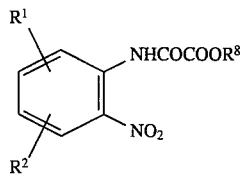

(VI)

wherein $R^1$, $R^2$ and $R^8$ have the meanings defined above, and cyclization of the compound to form a compound of the formula VII

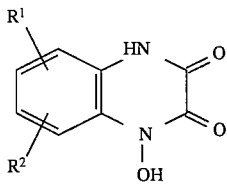

(VII)

wherein $R^1$ and $R^2$ have the meanings defined above, and reacting the compound with benzylhalogenide to form a compound of the formula VIII

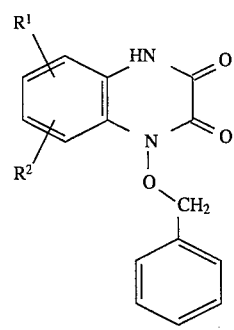

(VIII)

wherein $R^1$ and $R^2$ have the meanings defined above, and halogenating the compound to form a compound of the formula IX

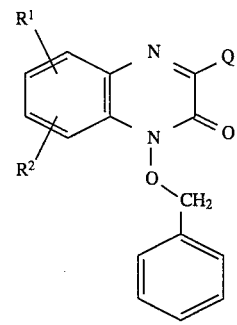

(IX)

wherein $R^1$ and $R^2$ have the meanings defined above and Q is Br, Cl or I, and reacting the compound with alkyl carbazate to form a compound with the formula X

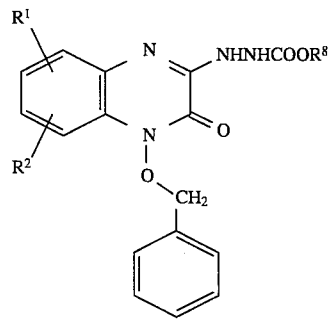

(X)

wherein $R^1$, $R^2$ and $R^8$ have the meanings defined above, and hydrogenolysis of the compound to form a compound of the formula XI

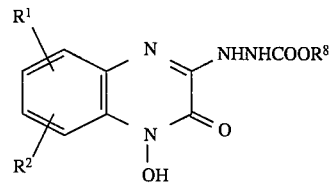

(XI)

wherein $R^1$, $R^2$ and $R^8$ have the meanings defined above, and then either thermal cyclization and simultaneous deoxygenation or basic cyclization under aqueous basic conditions and subsequent deoxygenation to form a compound of formula I, or b) halogenating a compound of the formula XII

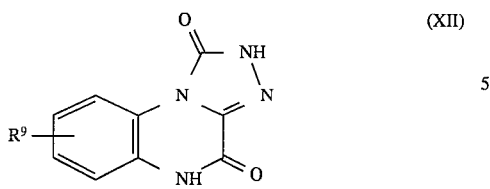

wherein $R^9$ is a 5- or 6-membered nitrogen-containing heterocyclic ring optionally mono-, di- or trisubstituted with one or more of phenyl and $C_{1-6}$-alkyl, or a fused ring system comprising a 5- or 6-membered nitrogen-containing heterocyclic ring optionally substituted with phenyl or $C_{1-6}$-alkyl, to form a compound of formula I, or c) nitrating a compound having the formula XII wherein $R^9$ has the meaning defined above to form a compound of formula I, or d) substituting a compound having the formula XIII

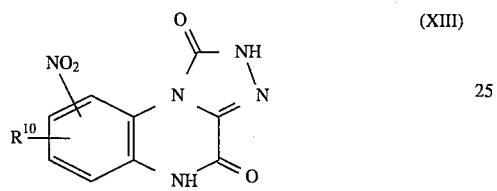

wherein $R^{10}$ is halogen or $C_{1-6}$-alkoxy with a 5- or 6-membered nitrogen-containing heterocyclic ring optionally mono-, di- or trisubstituted with one or more of phenyl and $C_{1-6}$-alkyl or a fused ring system comprising a 5- or 6-membered nitrogen-containing heterocyclic ring optionally substituted with phenyl or $C_{1-6}$-alkyl, to form a compound of formula I, or e) substituting a compound having the formula XIV

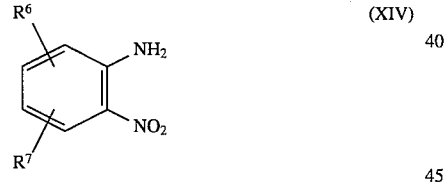

wherein one of $R^6$ and $R^7$ is halogen or $C_{1-6}$-alkoxy; and the other of $R^6$ and $R^7$ is hydrogen, $C_{1-6}$-alkyl, $C_{1-6}$-alkoxy, halogen, $NO_2$, $NH_2$, CN, $CF_3$, $COC_{1-6}$-alkyl or $SO_2NR'R''$, wherein R' and R" are independently hydrogen or $C_{1-6}$-alkyl, with a 5- or 6-membered nitrogen-containing heterocyclic ring optionally mono-, di- or trisubstituted with one or more of phenyl and $C_{1-6}$-alkyl or with a fused ring system comprising a 5- or 6-membered nitrogen-containing heterocyclic ring optionally substituted with phenyl or $C_{1-6}$-alkyl, to form a compound of the formula XV

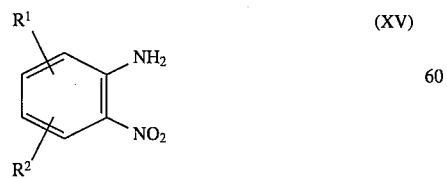

wherein $R^1$ and $R^2$ have the meanings defined above, and reacting the compound with an alkyl oxalylhalogenide to form a compound of the formula XVI

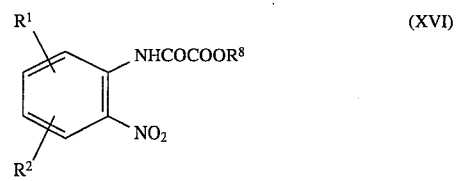

wherein $R^1$ and $R^2$ have the meanings defined above and $R^8$ is $C_{1-6}$-alkyl, and cyclization of the compound to form a compound of formula XVII

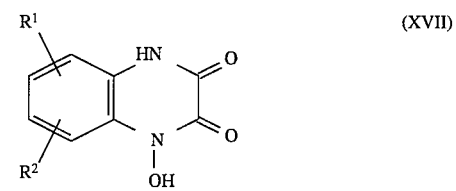

wherein $R^1$ and $R^2$ have the meanings defined above, and reacting the compound with benzylhalogenide to form a compound of the formula XVIII

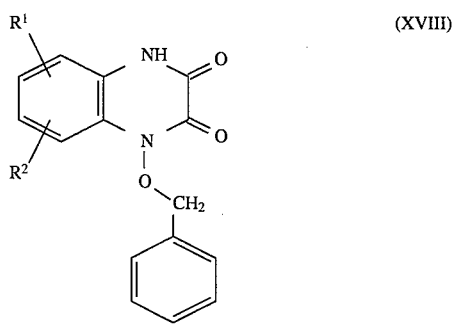

wherein $R^1$ and $R^2$ have the meanings defined above, and halogenating the compound to form a compound of the formula XIX

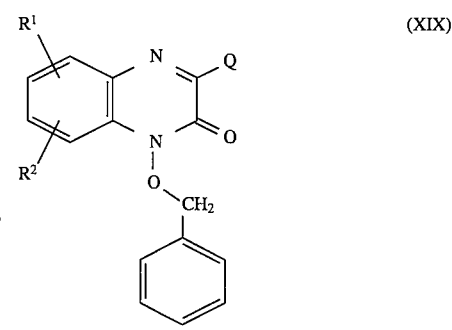

wherein $R^1$ and $R^2$ have the meanings defined above and Q is Br, Cl or I, and reacting the compound with alkyl carbazate to form a compound with the formula XX

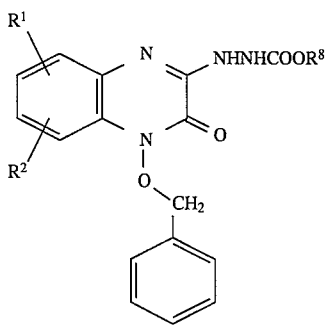

(XX)

wherein $R^1$, $R^2$ and $R^8$ have the meanings defined above, and hydrogenolysis of the compound to form a compound of the formula XXI

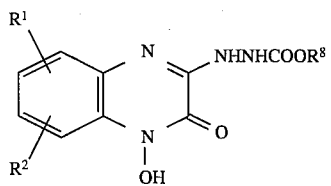

(XXI)

wherein $R^1$, $R^2$ and $R^8$ have the meanings defined above, and then either thermal cyclization and simultaneous deoxygenation or basic cyclization under aqueous basic conditions and subsequent deoxygenation to form a compound of formula I, f) reacting a compound of formula XIX with hydrazine hydrate to form a compound with the formula XXII

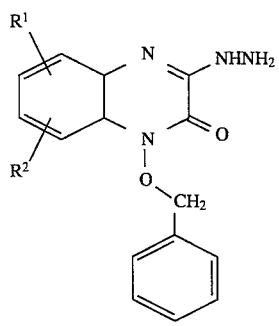

(XXII)

wherein $R^1$ and $R^2$ have the meanings defined above, and reacting the compound with phosgene or thiophosgene or a reactive equivalent thereof to form a compound of the formula XXIII

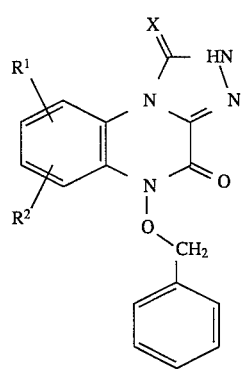

(XXIII)

wherein $R^1$, $R^2$ and X have the meanings defined above, and hydrolysis or hydrogenolysis of the compound to form a compound of formula XXIV

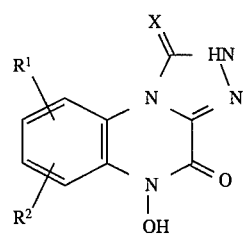

(XXIV)

wherein $R^1$, $R^2$ and X have the meanings defined above and deoxygenation to form a compound of formula I.

Pharmaceutically acceptable salts may be prepared according to standard procedures by treating a compound of formula I with the appropriate acids.

The starting materials for which the preparation is not described herein are either known compounds or compounds which may be prepared in analogy with the preparation of known compounds or in analogy with known methods.

The affinity of a substance for one or more of the different types of excitatory amino acid receptors may be studied in simple binding experiments. In essence, the method involves incubation of a particular selected radiolabelled ligand and the particular specific substance to be investigated with brain homogenate which contains the receptor. Measurement of receptor occupancy is made by determination of the radioactivity bound to the homogenate and subtraction of non-specific binding.

AMPA receptor binding may be studied by using $^3$H-AMPA as radioligand.

The influence of glutamic acid analogues on secondary effects of glutamate receptor interactions may be studied in vitro by using the phenomenon of spreading depression in chicken retina. Such experiments will provide information as to the efficacies (agonist/antagonist) of the test substances. This is in contrast to binding studies, which only provide information on the affinities of the compounds for the receptor.

The pharmacological properties of the compounds of the present invention can be illustrated by determining their capability for displacing radioactively labelled 2-amino-3-hydroxy-5-methyl-4-isoxazolepropionic acid (AMPA) from the AMPA type receptors. The antagonistic properties of the compounds is demonstrated by their capability to antagonize quisqualic acid stimulated spreading depression in chicken retina.

The displacement activity of the compounds may be shown by determining the $IC_{50}$ value which represents the concentration (μM) which causes a displacement of 50% of the specific binding of $^3$H-AMPA.

The antagonism is measured by determining the $IC_{50}$ value which represents the concentration which produces a 50% maximal inhibition of quisqualic acid stimulated spreading depression in chicken retina.

$^3$H-AMPA binding (Test 1)

500 μl of thawed rat cerebral cortical membrane homogenate in Tris-HCl (30 mM), $CaCl_2$ (2.5 mM) and KSCN (100 mM) pH 7.1 were incubated at 0° C. for 30 min. with 25 μl $^3$H-AMPA (5 nM final concentration) and the test compound and buffer. Nonspecific binding was determined by incubation with L-glutamic acid (600 μM final concentration). The binding reaction was terminated by adding 5 ml of ice-cold buffer followed by filtration through Whatman GF/C glass fibre filters and 2×5 ml wash with ice-cold buffer. Bound radioactivity was measured by scintillation counting. $IC_{50}$ was determined by Hill analysis of at least four concentrations of test compound.

Spreading depression (Test 2)

Chicks (3–10 days old) were decapitated, the eyes enucleated and sectioned along the equatorial plane. After removal of the anterior chamber and the vitreous body, the posterior chamber of each eye was placed in a small petri dish containing a physiological saline solution (P.S.S.) of the following composition (mM) NaCl (100), KCl (6.0), CaCl$_2$ (1.0), MgSO$_4$ (1.0), NaHCO$_3$ (30), NaH2PO$_4$ (1.0), glucose (20).

The solution was saturated with 100% O$_2$ and maintained at a temperature of 26° C.

The eyes were initially incubated in normal P.S.S. for 15–30 min. and then transferred to P.S.S. containing quisqualate (1 μg/ml). In this "stimulating solution" S.D.s start spontaneously usually from the edge of the retina, and can be easily observed by eye. The time taken for an S.D. to start in each eye was measured.

After a further 15 min. of incubation in normal P.S.S. the eyes were transferred to normal P.S.S. containing the test compound and incubated for 15 min. Thereafter the eyes were transferred to a "stimulating solution" containing the same concentration of the test compound. The time taken for an S.D. to start in each eye was measured again. The eyes were then placed back in normal P.S.S. and after 15 min. the time taken for S.D. to start was measured again, in order to assess the degree of recovery from any drug effects.

An increase in the time taken for S.D. to start of 30 seconds more than the control time is considered 100% inhibition of S.D. The drug effects therefore are expressed as the percentage maximum response obtained for a given dose. The test value can be quoted therefore as the concentration (μM) of test substance which produces a 50% maximal inhibition (IC$_{50}$). Test results obtained by testing some compounds of the present invention are shown in the following table 1.

TABLE 1

| Compound of example | TEST 1 IC$_{50}$ μM | TEST 2 IC$_{50}$ μM |
| --- | --- | --- |
| 1 | 0.18 | 3.9 |
| 2 | 1.7 | 4.8 |

The pharmaceutical preparations of compositions comprising the compounds of the invention may be administered to humans or animals by oral, rectal or parenteral route.

An effective amount of the active compound or a pharmaceutically acceptable salt thereof may be determined in accordance with the usual factors, such as the nature and severity of the condition and the weight of the mammal requiring treatment.

Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose, and polyvinylpyrrolidone.

The pharmaceutical preparations can be sterilized and mixed, if desired, with auxiliary agents, such as lubricants, preservatives, stabilizers, wetting agents, emulsifiers, salt for influencing osmotic pressure, buffers and/or colouring substances and the like, which do not deleteriously react with the active compounds.

Injectable solutions or suspensions, preferably aqueous solutions with the active compound dissolved in polyhydroxylated castor oil, are particularly suitable for parenteral administration.

Ampoules are convenient unit dosage forms.

Tablets, dragees, or capsules containing talc and/or a carrier or binder or the like are particularly suitable for oral administration. The carrier preferably is lactose and/or corn starch and/or potato starch.

A syrup, elixir, or the like can be used in the cases where a sweetened vehicle can be employed or is desired.

Generally, the compounds of this invention are dispensed in unit dosage form comprising 10–200 mg of active ingredient in or together with a pharmaceutically acceptable carrier per unit dosage.

The dosage of the compounds according to this invention is 1–500 mg/day, e.g. about 100 mg per dose, when administered to patients, e.g. humans, as a drug.

A typical tablet which may be prepared by conventional tabletting techniques contains:

| Core: | |
| --- | --- |
| Active compound (as free compound or salt thereof) | 100 mg |
| Colloidal silicon dioxide (Aerosil ®) | 1.5 mg |
| Cellulose, microcryst. (Avicel ®) | 70 mg |
| Modified cellulose gum (Ac-Di-Sol ®) | 7.5 mg |
| Magnesium stearate | 1 mg |
| Coating: | |
| HPMC | approx. 9 mg |
| *Mywacett ® 9-40T | approx. 0.9 mg |

*Acylated monoglyceride used as plasticizer for film-coating

The free compounds of the present invention which form alkali metal or alkaline earth metal salts may be employed in such salt form. Such alkali metal or earth alkali metal salts are ordinarily formed by reacting the compound with an equivalent amount or excess of the selected alkali metal or earth alkali metal as the hydroxide, frequently and suitably by admixture in the presence of a neutral solvent, from which the salt may be precipitated or recovered in other conventional manner, e.g. by evaporation. Administration of a compound of the invention is often preferably in the form of a pharmaceutically acceptable water-soluble alkali metal or earth alkali metal salt thereof, and orally, rectally, or parenterally in the form of a pharmaceutical composition wherein it is present together with a pharmaceutically acceptable liquid or solid carrier or diluent.

The compounds of the invention, together with a conventional adjuvant, carrier, or diluent, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical composition and unit dosage forms thereof may comprise conventional ingredients in conventional proportions, with or without additional active compounds or principles, and such unit dosage forms may contain any suitable effective AMPA antagonistic amount of the active ingredient commensurate with the intended daily dosage range to be employed. Tablets containing 10 mg to 200 mg of active ingredient or, more specified 50 mg, per tablet, are accordingly suitable representative unit dosage forms.

Due to their high degree of AMPA antagonistic activity and their low toxicity, together presenting a most favourable therapeutic index, the compounds of the invention may be administered to a subject, e.g. a living animal body, in need of such treatment, elimination, alleviation, or amelioration of an indication which is sensitive to a change in the AMPA receptor condition, e.g. sclerosis, Parkinsonism, Alzheimer's disease, Huntington's disease, epilepsy, deficiencies seen after ischemia, anoxia, hypoglycemia, head and spinal cord trauma, psychosis, muscle rigidity, emesis and analgesia, often preferably in the form of an alkali metal or earth alkali metal salt thereof, concurrently, simultaneously, or together with a pharmaceutically acceptable carrier or diluent, especially and preferably in the form of a pharmaceutical composition thereof, whether by oral, rectal, or parenteral (including subcutaneous) route, in an effective amount.

Suitable dosage ranges are 10–200 milligrams daily, preferably 50–100 milligrams daily, and especially 70–100 milligrams daily, depending as usual upon the exact mode of administration, form in which administered, the indication towards which the administration is directed, the subject involved and the body weight of the subject involved, and the preference and experience of the physician or veterinarian in charge.

Such method of treating may be described as the treatment of an indication caused by or related to hyperactivity of the excitatory neurotransmitters, and particularly the AMPA receptors in a subject in need thereof, which comprises the step of administering to the said subject a neurologically effective amount of an AMPA antagonistic compound of the invention, or a pharmaceutically acceptable salt thereof.

Furthermore, the present invention relates to the use of a compound of the invention for preparing a medicament for treating an indication caused by or related to hyperactivity of the excitatory neurotransmitters, and particularly the AMPA receptors in a subject in need thereof.

The invention will now be described in further detail with reference to the following examples:

EXAMPLE 1 a. 4-(1H-Imidazol-1-yl)-nitrobenzene

To a solution of 4-fluoronitrobenzene (25 g; ~0.18 mol) in 250 ml N,N-dimethylformamide was added imidazole (50 g; ~0.74 mol). The reaction mixture was stirred at 140° C. for 2 h, and then poured into ice-water to give the title compound as a precipitate. Yield: 32 g (~94%). M.p. 199°–202° C.

b. 4-(1H-Imidazol-1-yl)-aniline

A solution of 4-(1H-imidazol-1-yl)-nitrobenzene (20 g; ~0.11 mol) in a mixture of 500 ml ethyl acetate and 500 ml ethanol was hydrogenated in a Parr hydrogenation apparatus at 28.12 kPa (40 psi) and 25° C. by using 0.5 g 5% Pd-C as a catalyst. The reaction mixture was filtered and evaporated in vacuo to give the title compound (14 g) as crystals. M.p. 142°–144° C.

c. 1-Ethoxalylamino-4-(1H-imidazol-1-yl)-benzene

To a solution of 4-(1H-imidazol-1-yl)-aniline (14 g; ~88.2 mmol) in 400 ml dry tetrahydrofuran was added dry triethylamine (14.0 ml; ~102 mmol). Ethoxalyl chloride (11.2 ml; 100 mmol) was added dropwise and the reaction mixture was stirred for 2 h. The solvent was removed under reduced pressure, and the residue was stirred with water to give the title compound (19.2 g; 85%). M.p. 177°–180° C.

d. 2-Ethoxalylamino-5-(1H-imidazol-1-yl)-nitrobenzene

1-Ethoxalylamino-4-(1H-imidazol-1-yl)-benzene (16 g; 61.8 mmol) was added gradually to 100 ml nitric acid (d=1.52) at 0° C. Stirring was continued at 0° C. for 1 h, and then the reaction mixture was poured into ice-water to give the title compound (18 g; 80%) as a nitric acid salt. M.p. 180° C. (decomp.).

e. 6-(1H-Imidazol-1-yl)-4-hydroxyquinoxaline-2,3(1H,4H)-dione

A solution of 2-ethoxalylamino-5-(1H-imidazol-1-yl)-nitrobenzene (18 g; ~49 mmol) (as a nitric acid salt) in 500 ml ethyl acetate and 500 ml ethanol was hydrogenated in a Parr hydrogenation apparatus at 28.12 kPa (40 psi) by using 1 g 5% Pd-C as a catalyst.

The precipitated product and the catalyst was filtered off and washed with ethyl acetate. The filter cake was washed several times with 5% aqueous potassium hydroxide. Neutralization (ph~6) of the filtrate with 4N hydrochloric acid gave the title compound (11 g; 92%). M.p. 300° C. (decomp.).

f. 4-Benzyloxy-6-(1H-imidazol-1-yl)-quinoxaline-2,3(1H,4H)-dione

To a solution of 6-(1H-imidazol-1-yl)-4-hydroxyquinoxaline-2,3(1H,4H)-dione (10.4 g; ~42.6 mmol) in 500 ml 1M potassium dihydrogen phosphate buffer pH 7.4, was added 500 ml ethanol and then 15.0 ml (~126 mmol) benzylbromide. Stirring was continued at 25° C. overnight. The precipitate was filtered off and washed with ethanol to give the title compound (9.8 g; 69%). M.p. 230° C. (decomp.).

g. 4-Benzyloxy-2-chloro-6-(1H-imidazol-1-yl)-quinoxalin-3(4H)-one

A solution of 20% phosgene in toluene (57 ml; 118 mmol) was added to a stirred solution of 4-benzyloxy-6-(1H-imidazol-1-yl)-quinoxaline-2,3(1H,4 H)-dione (9.2 g; 27.5 mmol) in 200 ml dry N,N-dimethylformamide at 0° C. The mixture was stirred at 25° C. overnight and then evaporated in vacuo. The residue was stirred with ice-cooled water and 4N sodium hydroxide was added until pH was about 6 which resulted in the title compound (9.5 g; 98%) as a precipitate. M.p. 140° C. (decomp.).

h. 4-Benzyloxy-2-(2-ethoxycarbonylhydrazino)-6-(1H-imidazol-1-yl)-quinoxalin-3(4H)-one To a solution of 4-benzyloxy-2-chloro-6-(1H-imidazol-1-yl)-quinoxalin-3(4 H)-one (9.4 g; ~27.6 mmol) in 500 ml acetonitrile was added ethyl carbazate (28 g; ~270 mmol). The reaction mixture was refluxed overnight. Cooling to room temperature gave the title compound (11.1 g; 99%) as a precipitate. M.p. 197°–199° C.

i. 2-(2-Ethoxycarbonylhydrazino)-4-hydroxy-6-(1H-imidazol-1-yl)-quinoxalin-3(4H)-one A solution of 4-benzyloxy-2-(2-ethoxycarbonylhydrazino)-6-(1H-imidazol-1-yl)-quinoxalin-3(4H)-one (10.9 g; ~25.9 mmol) in a mixture of 200 ml N,N-dimethylformamide and 100 ml water was hydrogenated at atmospheric pressure and room temperature by using 1 g 5% Pd-C as a catalyst. The catalyst was removed by filtration, and the residue was stirred with acetone to give the title compound (7.9 g; 92%). M.p. 216°–218° C. (decomp.).

j. 7-(1H-Imidazol-1-yl)[1,2,4]triazolo[4,3-a]quinoxaline-1,4(2H,5H)-dione.

To a solution of 2-(2-ethoxycarbonylhydrazino)-4-hydroxy-6-(1H-imidazol-1-yl)quinoxalin-3(4 H)-one (7.8 g; ~23.6 mmol) in 250 ml dry N,N-dimethylformamide was added triphenylphosphine (18.5 g; ~70.6 mmol). Stirring of the mixture was continued overnight at 140° C. followed by evaporation in vacuo. The residue was stirred with dichloromethane to give the title compound (5.7 g; 90%). M.p.>300° C.

$^1$H-NMR (DMSO-$d_6$): δ12.5 (2H, broad s), 8.6 (1H, d, J=9.2 Hz), 8.15 (1H, s), 7.65 (1H, s), 7.5 (1H, dd, J=9.2 Hz and 2.5 Hz), 7.35 (1H, d, J=2.5 Hz), 7.15 (1H, s).

EXAMPLE 2

7-(1H-Imidazol-1-yl)-8-trifluoromethyl[1,2,4]triazolo[4,3-a]quinoxaline-1,4(2H,5H)-dione The title compound was prepared from 2-fluoro-5-nitrobenzotrifluoride and imidazole by a method analogous to the method described in example 1 . M.p.>300° C. (decomp.).

$^1$H-NMR (DMSO-d6): $\delta$12.8 (2H, broad s), 8.95 (1H, s), 7.85 (1H, s), 7.45 (1H, s), 7.25 (1H, s), 7.10 (1H, s).

EXAMPLE 3

8-Bromo-7-(1H-imidazol-1-yl)[1,2,4]triazolo[4,3-a]quinoxaline-1,4(2H,5H)-dione

To a solution of 0.94 g (~3.5 mmol) of 7-(1H-Imidazol-1-yl)[1,2,4]triazolo [4,3-a]quinoxaline-1,4(2H,5H)-dione in 7.5 ml concentrated (95–97%) sulfuric acid was added first 1.22 g (~3,9 mmol) silver sulfate and then 0.2 ml (~3,9 mmol) bromine. Stirring was continued at 24° C. for 48 h. The reaction mixture was filtered from silver bromide and then poured into 40 ml ice-water. The precipitate was filtered off to give a crude product. To a solution of the crude product in water was added 4N sodium hydroxide to pH=6 to give the title compound as a precipitate (0.42 g; 35%). M.p.>300° C. (decomp.).

$^1$H-NMR (DMSO-d$_6$): $\delta$13.0 (1H, broad s), 12.0 (1H, broad s), 8.75 (1H, s), 7.90 (1H, s), 7.45 (1H, s), 7.15 (1H, s), 7.10 (1H, s).

EXAMPLE 4 a. 4-Amino-2-(2-methyl-1H-imidazol-1-yl)-5-nitrobenzotrifluoride

To a solution of 20.0 g (~83 mmol) 4-amino-2-chloro-5-nitrobenzotrifluoride in 50 ml dry N,N-dimethylformamide was added 30 g (~370 mmol) 2-methylimidazole, and stirring was continued at 180° C. for 30 h. The reaction mixture was poured into 400 ml water to give the title compound (14.7 g; 62%). M.p. 222°–225° C.

b. 4-Ethoxalylamino-2-(2-methyl-1H-imidazol-1-yl)-5-nitrobenzotrifluoride

To a solution of 14.5 g (~50.7 mmol) of 4-amino-2-(2-methyl-1H-imidazol-1 -yl)-5-nitrobenzotrifluoride in 200 ml dry pyridine was added dropwise 11,3 ml (~102 mmol) ethoxalyl chloride, and stirring was continued overnight at room temperature. The reaction mixture was filtered and the filtrate was evaporated to give the title compound as a crude oil (19 g).

c. 1-Hydroxy-6-(2-methyl-1H-imidazol-1-yl)-7-trifluoromethylquinoxaline-2,3(1 H,4H)-dione A solution of 19 g crude 4-ethoxalylamino-2-(2-methyl-1H-imidazol-1-yl)-5 -nitrobenzotrifluoride in 500 ml 96% ethanol was hydrogenated in a Parr hydrogenation apparatus at 28.12 kPa (40 psi) by using 2 g 5% Pd-C as a catalyst. The catalyst plus precipitated product was filtered off and washed with ethanol. The filter cake was washed several times with 1N aqueous potassium hydroxide. The combined aqueous filtrates were added 4N hydrochloric acid to pH=4 to give the title compound (9.5 g; 58%). M.p.>300° C.

d. 1 -Benzyloxy-6-(2-methyl-1H-imidazol-1-yl)-7-trifluoromethylquinoxaline-2,3(1H,4H)-dione To a solution of 5.3 g (~16.3 mmol) of 1-hydroxy-6-(2-methyl-1H-imidazol-1 -yl)-7-trifluoromethylquinoxaline-2,3(1H,4H)-dione in a mixture of 80 ml ethanol and 80 ml 1M potassium dihydrogen phosphate buffer pH 7.4 was added 2.1 ml (17.7 mmol) benzylbromide. Stirring was continued at 25° C. for 1 h. The precipitate was filtered off and washed with water and a little ice-cooled ethanol to give the title compound (5.2 g; 78%). M.p. 156° C. (decomp.).

e. 1-Benzyloxy-3-(2-ethoxycarbonylhydrazino)-6-(2-methyl-1H-imidazol-1-yl)-7-trifluoromethylquinoxalin-2(1H)-one A solution of 20% phosgene in toluene (18.5 ml; 35.7 mmol) was added dropwise to a stirred solution of 4.85 g (~11.7 mmol) 1-benzyloxy-6-(2 -methyl-1H-imidazol-1-yl)-7-trifluoromethylquinoxaline-2,3(1H,4H)-dione in 75 ml dry N,N-dimethylformamide at 25° C. The mixture was stirred at 25° C. overnight and then evaporated in vacuo to give the 3-chloro derivative as an oil. To a solution of this crude product in 75 ml acetonitrile was added 14.5 g (~140 mmol) ethyl carbazate. The reaction mixture was refluxed for 3 h. Cooling in an ice-bath gave the title compound (2.0 g; 35%) as a precipitate. M.p. 232° C. (decomp.).

f. 3-(2-Ethoxycarbonylhydrazino)-1-hydroxy-6-(2-methyl-1H-imidazol-1 -yl)-7-trifluoromethylquinoxalin-2(1H)-one A solution of 1.4 g (~2.8 mmol) 1-benzyloxy-3-(2-ethoxycarbonylhydrazino)-6-(2-methyl-1H-imidazol-1-yl)-7-trifluoromethylquinoxalin-2(1H)-one in a mixture of 100 ml ethanol and 50 ml N,N-dimethylformamide was hydrogenated at atmospheric pressure by using 0.15 g 5% Pd-C as a catalyst. The catalyst was removed by filtration, and the filtrate was evaporated in vacuo to give the title compound as a crude product (1 g).

g. 8-(2-Methyl-1H-imidazol-1-yl)-7-trifluoromethyl[1,2,4]triazolo[4,3 -a]quinoxaline-1,4(2H ,5H)-dione To a solution of 1 g crude 3-(2-ethoxycarbonylhydrazino)-1-hydroxy-6-(2 -methyl-1H-imidazol-1-yl)-7-trifluoromethylquinoxalin-2(1H)-one in 50 ml dry N,N-dimethylformamide was added 1.05 g (~4.0 mmol) triphenylphosphine. Stirring was continued at 130° C. for 17 h followed by evaporation in vacuo. Column chromatography (silica gel; eluent: dichloromethane containing 10% methanol) gave the title compound (0.7 g; 75%). M.p. 375° C. (decomp.).

$^1$H-NMR (DMSO-d$_6$): $\delta$13.0 (2H, broad s), 8.45 (1H, s), 7.70 (1H, s), 7.20 (1H, s), 6.95 (1H, s), 2.05 (3H, s). MS (M/e): 350 (M$^+$, 100%).

EXAMPLE 5

8-(4-Methyl-1H-imidazol-1-yl)-7-trifluoromethyl[1,2,4]triazolo-[4,3-a]quinoxaline-1,4(2H,5H)-dione The title compound was prepared from 4-amino-2-chloro-5-nitrobenzotrifluoride and 4-methylimidazole by a method analogous to the method described in example 4. M.p. 320° C. (decomp.).

$^1$H-NMR (DMSO-d$_6$): $\delta$12.5 (2H, broad s), 8.50 (1H, s), 7.70 (1H, s), 7.65 (1H, s), 7.10 (1H, s), 2.20 (3H, s). MS (m/e): 350 (M$^+$, 100%).

EXAMPLE 6

8-(1H-Imidazol-1-yl)-7-trifluoromethyl[1,2,4]triazolo[4,3-a]quinoxaline-1,4(2H,5H)-dione The title compound was prepared from 4-amino-2-chloro-5-nitrobenzotrifluoride and imidazole by a method analogous to the method described in example 4. (M.p. 350° C. (decomp.).

$^1$H-NMR (DMSO-d$_6$): $\delta$13.1 (1H, broad s), 12.1 (1H, broad s), 8.50 (1H, s), 7.85 (1H, s), 7.70 (1H, s), 7.40 (1H, s), 7.10 (1H, s). MS (m/e): 336 (M$^+$, 100%).

EXAMPLE 7

8-Morpholino-7-trifluoromethyl[1,2,4]triazolo[4,3-a]quinoxaline-1,4(2H,5H)-dione The title compound was prepared from 4-amino-2-chloro-5-nitrobenzotrifluoride and morpholine by a method analogous to the method described in example 4. M.p.>300° C.

$^1$H-NMR (DMSO-d$_6$): δ13.0 (1H, broad s), 12.0 (broad s), 8.75 (1H, s), 7.50 (1H, s), 3.70 (4H, m), 2.80 (4H, m). MS (m/e): 355 (M$^+$, 70%).

EXAMPLE 8

8-Piperidino-7-trifluoromethyl[1,2,4]triazolo[4,3-a]quinoxaline-1,4(2H,5H)-dione The title compound was prepared from 4-amino-2-chloro-5-nitrobenzotrifluoride and piperidine by a method analogous to the method described in example 4. M.p.>300° C. (decomp.).

$^1$H-NMR (DMSO-d6): δ13.0 (2H, broad s), 8.75 (1H, s), 7.50 (1H, s), 2.80 (4H, m), 1.65 (4H, m), 1.55 (2H,m).

EXAMPLE 9

8-(4-Methylpiperazin-1-yl)-7-trifluoromethyl[1,2,4]triazolo[4,3-a]quinoxaline-1,4(2H,5H)-dione The title compound was prepared from 4-amino-2-chloro-5-nitrobenzotrifluoride and 1-methylpiperazine by a method analogous to the method described in example 4. M.p.>300° C.

$^1$H-NMR (DMSO-d$_6$): δ13.0 (2H, broad s), 8.65 (1H, s), 7.50 (1H, s), 2.70 (4H, m), 2.45 (4H, m), 2.20 (3H, s).

EXAMPLE 10 a. 8-(2,4-Dimethyl-1H-imidazol-1-yl)-7-trifluoromethyl[1,2,4]triazolo-[4,3-a]quinoxaline-1,4(2H,5H)-dione The title compound was prepared from 4-amino-2-chloro-5-nitrobenzotrifluoride and 2,4-dimethylimidazole by a method analogous to the method described in example 4. M.p.>330° C.

$^1$H-NMR (DMSO-d6): δ2.02 (s, 3H), 2.11 (s, 3H), 6.91 (s, 1H), 7.69 (s, 1H), 8.44 (s, 1H), 12.15 (br.s, 1H), 13.15 (br. s, 1H). MS (m/e): 364 (M$^+$, 100%).

b. 8-(2,4-Dimethyl-1H-imidazol-1-yl)-7-trifluoromethyl[1,2,4]triazolo-[4,3-a]quinoxaline-1,4(2H,5H)-dione, hydrochloride The free base prepared in the above example 10a was stirred with 37% hydrochloric acid for 1 h at 0° C. The precipitated hydrochloride was isolated by filtration and washed with acetone. Recrystallization from water gave the pure title compound. M.p.>275° C. decomp.

$^1$H-NMR (DMSO-d$_6$): δ2.30 (s, 3H), 2.34 (s, 3H), 7.59 (s, 1H), 7.87 (s, 1H), 8.83 (s, 1H), 12.42 (s, 1H), 13.3 (s, 1H).

EXAMPLE 11 a. 8-Fluoro[1,2,4]triazolo[4,3-a]quinoxaline-1,4(2H,5H)-dione

The title compound was prepared from 5-fluoro-2-nitroaniline by a method analogous to the method described in example 1, except that the fluorine was not displaced by a nitrogen-containing heterocyclic ring.

$^1$H-NMR (DMSO-d$_6$): δ13,0 (1H, s), 11.9 (1H, s), 8.3 (1H,dd), 7.2 (2H, m).

b. 8-Fluoro-7-nitro[1,2,4]triazolo[4,3-a]quinoxaline-1,4(2H,5H)-dione

To a solution of 2.51 g (~11.4 mmol) of 8-fluoro[1,2,4]triazolo[4,3-a]quinoxalic-1,4(2H,5H)-dione in 15 ml concentrated (95-97%) sulfuric acid was added 1.27 g (12.6 mmol) potassium nitrate. Stirring was continued at 25° C. for 30 min. The reaction mixture was poured into ice-water to give the title compound as a precipitate (2.0 g; 66%).

$^1$H-NMR (DMSO-d$_6$): δ13.2 (1H, s), 12.0 (1H, s), 8.5 (1H, d), 8.0 (1H, d).

c. 8-(1H-Imidazol-1-yl)-7-nitro[1,2,4]triazolo[4,3-a]quinoxaline-1,4(2H,5H)-dione To a solution of 0.5 g (~1.89 mmol) 8-fluoro-7-nitro[1,2,4]triazolo[4,3 -a]quinoxaline-1,4(2H,5H)-dione in 10 ml dry N,N-dimethylformamide was added 0.4 g (~5.9 mmol) imidazole. The reaction mixture was stirred at 120° C. for 2h. Evaporation in vacuo gave the title compound as an oil, which was solidified by stirring with water. Yield: 0.34 g (58%). M.p.>300° C. decomp.

$^1$H-NMR (DMSO-d$_6$+D$_2$O): δ8.60 (1H, s), 7.97 (1H, s), 7.93 (1H, s), 7.45 (1H, s), 7.15 (1H, s).

EXAMPLE 12

7-Nitro-8-thiomorpholino[1,2,4 ]triazolo[4,3-a]quinoxaline-1,4(2H,5H)-dione

The title compound was prepared from 8-fluoro-7-nitro[1,2,4]triazolo[4,3 -a]quinoxaline-1,4(2H,5H)-dione and thiomorpholine by a method analogous to the method described in example 11. M.p. 230° C. decomp.

$^1$H-NMR (DMSO-d$_6$): δ12.9 (1H, broad s), 12.0 (1H, broad s), 8.45 (1H, s), 7.75 (1H, s), 3.25 (4H, t), 2.80 (4H, t).

EXAMPLE 13

8-(4-Phenyl-1H-imidazol-1-yl)-7-nitro[1,2,4]triazolo[4,3-a]quinoxaline-1,4-(2H,5H)-dione The title compound was prepared from 8-fluoro-7-nitro[1,2,4]triazolo[4,3 -a]quinoxaline-1,4(2H,5H)-dione and 4-phenylimidazole by a method analogous to the method described in example 11. M.p. 365° C. (decomp.).

$^1$H-NMR (DMSO-d$_6$): δ12.8 (2H, broad s), 8.70 (1H, s), 8.05 (1H, s), 8.0 (1H, s), 7.95 (2H, d), 7.8 (2H, d), 7.4 (2H, t), 7.3 (1H, t).

EXAMPLE 14

8-Morpholino-7-nitro[1,2,4]triazolo[4,3-a]quinoxaline-1,4(2H,5H)-dione

The title compound was prepared from 8-fluoro-7-nitro[1,2,4]triazolo[4,3 -a]quinoxaline-1,4(2H,5H)-dione and morpholine by a method analogous to the method described in example 11. M.p. 250° C. decomp.

$^1$H-NMR (DMSO-d$_6$): δ12.4 (2H, broad s), 8.45 (1H, s), 7.75 (1H, s), 3.7 (4H, t), 2.95 (4H, t).

EXAMPLE 15

8-(2-Isopropyl-1H-imidazol-1-yl)-7-nitro[1,2,4]triazolo[4,3-a]quinoxaline-1,4(2H,5H)-dione The title compound was prepared from 8-fluoro-7-nitro[1,2,4]triazolo[4,3 -a]quinoxaline-1,4(2H,5H)-dione and 2-isopropylimidazole by a method analogous to the method described in example 11. M.p. 240° C. decomp.

¹H-NMR (DMSO-d₆): δ12.75 (2H, broad s), 8.55 (1H, s), 8.05 (1H, s), 7.20 (1H, d), 6.95 (1H, d), 2.65 (1H, m), 1.10 (6H, d).

EXAMPLE 16

8-(2-n-Propyl-1H-imidazol-1-yl)-7-nitro[1,2,4]triazolo[4,3-a]quinoxaline-1,4(2H,5H)-dione The title compound was prepared from 8-fluoro-7-nitro [1,2,4]triazolo[4,3 -a]quinoxaline-1,4(2H,5H)-dione and 2-n-propylimidazole by a method analogous to the method described in example 11. M.p. 260° C. decomp.

¹H-NMR (DMSO-d6): δ13.3 (1H, s), 12.3 (1H, s), 8.50 (1H, s), 8.05 (1H, s), 7.25 (1H, d), 7.00 (1H, d), 2.35 (2H, t), 1.55 (2H, q), 0.85 (3H, t).

EXAMPLE 17

8-(1H-Benzimidazol-1-yl)-7-nitro[1,2,4]triazolo[4,3-a] quinoxalin-1,4(2H,5H)-dione The title compound was prepared from 8-fluoro-7-nitro [1,2,4]triazolo[4,3 -a]quinoxaline-1,4(2H,5H)-dione and benzimidazole by a method analogous to the method described in example 11. M.p.>300° C. decomp.

¹H-NMR (DMSO-d₆): δ12.7 (2H, broad s), 8.70 (1H, s), 8.55 (1H, s), 8.15 (1H, s), 7.80 (1H, m), 7.30 (4H, m).

EXAMPLE 18 a. 2,4-Difluoro-5-nitrobenzotrifluoride

A mixture of 100 g of 2,4-dichloro-5-nitrobenzotrifluoride and 89,5 g of potassium fluoride was dried by azeotropic distillation with toluene on the evaporator. Then 200 ml of dry N,N-dimethylformamide was added, and the mixture was heated at 150° C. for about 12 h under nitrogen. To the cooled mixture was added 300 ml of water and 200 ml of ethyl acetate. The solution was decanted from the inorganic residue, which was then washed with ethyl acetate. The combined organic phase was washed with 3×100 ml of brine and 100 ml of water and finally dried with anhydrous sodium sulphate. The filtered solution was evaporated to dryness. Distillation of the crude oil gave 62 g (70%) of the title compound.

¹H-NMR (CDCl₃): δ7.25 (t, 1H), 8.49 (t, 1H).

b. 4-Amino-2-fluoro-5-nitrobenzotrifluoride 61 g (269 mmol) of 2,4-difluoro-5-nitrobenzotrifluoride was added dropwise to 500 ml of 25% ammonium hydroxide with stirring on an ice-bath. The mixture was stirred at room temperature overnight and filtered. The precipitate was washed with water and dried to give 55.5 g (92%) of the title compound. M.p. 139°–141° C.

¹H-NMR (DMSO-d₆): δ6.97 (d, 1H), 8.1 (br. s, 2H), 8.30 (d, 1H).

c. 8-(2-Ethyl-4-methyl-1H-imidazol-1-yl)-7-trifluoromethyl [1,2,4]triazolo-[4,3-a]quinoxaline-1,4(2H,5H)-dione, hydrochloride The title compound was prepared from 4-amino-2-fluoro-5-nitrobenzotrifluoride and 2-ethyl-4-methylimidazole by a method analogous to the method described in example 10. M.p. 281°–283° C.

¹H-NMR (DMSO-d₆): δ1.22 (t, 3H), 2.34 (s, 3H), 2.55–2.72 (m, 2H), 7.60 (s, 1H), 7.89 (s, 1H), 8.81 (s, 1H), 12.48 (s, 1H), 13.28 (s, 1H).

EXAMPLE 19

8-(2-n-Propyl-1H-imidazol-1-yl)-7-trifluoromethyl [1,2,4]triazolo[4,3-a]quinoxaline-1, 4(2H,5H)-dione, hydrochloride The title compound was prepared from 4-amino-2-fluoro-5-nitrobenzotrifluoride and 2-n-propylimidazole by a method analogous to the method described in example 10. M.p.>300° C.

¹H-NMR (DMSO-d6): δ0.86 (t, 3H), 1.55–1.79 (m, 2H), 2.65 (t, 2H), 7.83 (d, 1H), 7.87 (s, 1H), 7.91 (br.s, 1H), 8.82 (s, 1H), 12.44 (s, 1H), 13.30 (s, 1H).

EXAMPLE 20

8-(2-Isopropyl-1H-imidazol-1-yl)-7-trifluoromethyl [1,2,4]triazolo[4,3-a]quinoxaline-1,4(2H,5H)-dione The title compound was prepared from 4-amino-2-fluoro-5-nitrobenzotrifluoride and 2-isopropylimidazole by a method analogous to the method described in example 4. M.p. 340° C. decomp.

¹H-NMR (DMSO-d6): δ12.70 (2H, broad s), 8.50 (1H, s), 7.70 (1H, s), 7.15 (1H, d), 6.95 (1H, d), 2.55 (1H, m), 1.15 (3H, d), 1.10 (3H, d).

EXAMPLE 21

8-(4-Methyl-2-phenyl-1H-imidazol-1-yl)-7-trifluoromethyl[1,2,4]triazolo-[4,3-a] quinoxaline-1,4(2H,5H)-dione, hydrochloride The title compound was prepared from 4-amino-2-fluoro-5-nitrobenzotrifluoride and 4-methyl-2-phenylimidazole by a method analogous to the method described in example 10. M.p. 296° C. decomp.

¹H-NMR (DMSO-d₆): δ2.43 (s, 3H), 7.4–7.6 (m, 5H), 7.77 (s, 1H), 7.80 (s, 1H), 8.92 (s, 1H), 12.41 (s, 1H), 13.98 (s, 1H).

EXAMPLE 22

7-Chloro-8-(2-ethyl-4-methyl-1H-imidazol-1-yl)[1,2,4] triazolo[4,3-a]quinoxaline-1,4(2H,5H)-dione The title compound was prepared from 1,2,4-trichloro-5-nitrobenzene and 2 -ethyl-4-methylimidazole by a method analogous to the method described in example 18, except that the product was isolated as the free base. M.p. 273°–275° C.

¹H-NMR (DMSO-d₆): δ1.09 (t, 3H), 2.12 (s, 3H), 2.36 (q, 2H), 6.87 (br. s, 1H), 7.44 (s, 1H), 8.49 (s, 1H).

EXAMPLE 23 a. 4-Amino-2-fluoro-5-nitrobenzonitrile 20 g (108 mmol) of 2,4-difluoro-5-nitrobenzonitrile was added to 200 ml of 25% ammonium hydroxide and the mixture was stirred for 90 min. at room temperature. The yellow precipitate was isolated by filtration and washed with water and a small amount of cold ethanol to give 18.8 g (96%) of the title compound. M.p. 197°–199° C.

¹H-NMR (DMSO-d₆): δ6.90 (d, 1H), 8.27 (br. s, 2H), 8.62 (d, 1H).

b. 7-Cyano-8-(1H-imidazol-1-yl)[1,2,4]triazolo[4,3-a]quinoxaline-1,4 -(2H,5H)-dione The title compound was prepared from 4-amino-2-fluoro-5-nitrobenzonitrile and imidazole by a method analogous to the method described in example 4. M.p.>300° C.

$^1$H-NMR (DMSO-d6): δ7.18 (s, 1H), 7.62 (s, 1H), 7.69 (s, 1H), 8.09 (s, 1H), 8.67 (s, 1H), 12.25 (br. s, 1H), 13.20 (hr. s, 1H). IR (KBr): 2233 cm$^{-1}$ (CN).

EXAMPLE 24

7Cyano-8-(2-ethyl-4-methyl-1H-imidazol-1-yl)[1,2,4]triazolo[4,3-a]quinoxaline-1,4(2H,5H)-dione, hydrochloride The title compound was prepared from 4-amino-2-fluoro-5-nitrobenzonitrile and 2-ethyl-4-methylimidazole by a method analogous to the method described in example 10. M.p.>270° C. decomp.

$^1$H-NMR (DMSO-d6): δ1.25 (t, 3H), 2.37 (s, 3H), 2.77 (q, 2H), 7.70 (s, 1H), 7.91 (s, 1H), 8.88 (s, 1H), 12.50 (s, 1H), 13.3 (s, 1H).

EXAMPLE 25 a. 1-Benzyloxy-3-chloro-6-(1H-imidazol-1-yl)-7-trifluoromethylquinoxalin-2(1H)-one A solution of 20% phosgene in toluene (50 ml, 96 mmol) was added dropwise to a stirred solution of 12.1 g (30 mmol) of 1-benzyl-6-(1H-imidazol- 1-yl)-7-trifluoromethylquinoxaline-2,3(1H,4H)-dione in 100 ml of dry N,N-dimethylformamide at room temperature. The mixture was stirred at room temperature overnight and neutralized by cautious addition of 16 g (190 mmol) of sodium hydrogen carbonate. After 10 min. the mixture was poured into 500 ml of water. Light petroleum (200 ml) was added under vigorous stirring and the solid formed was isolated by filtration. The product was washed with water and ether and dried in vacuo to give 11.0 g (87%) of crude title compound.

$^1$H-NMR (DMSO-d6): δ5.37 (s, 2H), 7.16 (s, 1H), 7.4–7.65 (m, 5H), 7.70 (s, 1H), 7.94 (s, 1H), 8.15 (s, 1H).

b. 1-Benzyloxy-3-hydrazino-6-(1H-imidazol-1-yl)-7-trifluoromethylquinoxalin-2(1H)-one Hydrazine hydrate (2.7 ml, 55 mmol) was added to a solution of 5.9 g (14 mmol) of 1-benzyloxy-3-chloro-6-(1H-imidazol-1-yl)-7-trifluoromethylquinoxalin-2(1H)-one in 100 ml of dichloromethane with stirring at 0° C. After 1 h the mixture was evaporated to dryness and the residue was triturated with water and dried to give 5.3 g (90%) of crude title compound.

$^1$H-NMR (DMSO-d6): δ5.32 (s, 2H), 7.09 (s, 1H), 7.3–7.6 (m, 8H), 7.79 (s, c. 5-Benzyloxy-8-(1H-imidazol-1-yl)-1-thioxo-7-trifluoromethyl[1,2,4]triazolo[4,3-a]quinoxalin-4(5H)-one A solution of thiophosgene (1.1 ml, 14 mmol) in 10 ml of dry tetrahydrofuran was added dropwise to a stirred solution of 2.91 g (7 mmol) of 1-benzyloxy-3-hydrazino-6-(1H-imidazol-1-yl)-7-trifluoromethylquinoxalin-2(1H)-one in a mixture of 100 ml of dry tetrahydrofuran and 25 ml of dry N,N-dimethylformamide at 0° C. The mixture was stirred for 2h at 0° C. and evaporated to dryness. The solid residue was suspended in 100 ml of water, neutralized with solid sodium hydrogen carbonate and filtered. Recrystallization from ethanol afforded 1.64 g (51%) of the title compound.

$^1$H-NMR (DMSO-d6): δ5.32 (s, 2H), 7.19 (s, 1H), 7.4–7.6 (m, 5H), 7.72 (s, 1H), 7.95 (s, 1H), 10.44 (s, 1H).

d. 5-Hydroxy-8-(1H-imidazol-1-yl)-1-thioxo-7-trifluoromethyl[1,2,4]triazolo[4,3-a]quinoxalin-4(5H)-one A solution of 1.38 g (3 mmol) of 5-benzyloxy-8-(1H-imidazol-1-yl)-1-thioxo-7 -trifluoromethyl[1,2,4]triazolo[4,3-a]quinoxalin-4(5H)-one in 20 ml of conc. sulfuric acid was stirred at room temperature for 20 min., and poured into 200 ml of ice-water. The stirred mixture was adjusted to pH 5–6 by cautious addition of solid sodium hydroxide at 0° C. Extraction with ethyl acetate (5×100 ml) gave 270 mg (25%) of the title compound.

$^1$H-NMR (DMSO-d$_6$): δ7.16 (s, 1H), 7.49 (s, 1H), 7.94 (s, 1H), 8.00 (s, 1H), 10.44 (s, 1H).

e. 8-(1H-imidazol-1-yl)-1-thioxo-7-trifluoromethyl[1,2,4]triazolo[4,3 -a]quinoxalin-4(5H)-one A solution of 250 mg (0.67 mmol) of 5-hydroxy-8-(1H-imidazol-1-yl)-1-thioxo-7-trifluoromethyl[1,2,4]triazolo[4,3-a]quinoxalin-4(5H)-one and 360 mg (1.37 mmol) of triphenylphosphine was stirred at 140° C. for 20 h. The solution was evaporated to dryness, and the solid residue was triturated with small portions of cold dichloromethane to give the crude product. Recrystallization from ethanol gave 90 mg (40%) of pure title compound. M.p.>300° C.

$^1$H-NMR (DMSO-d$_6$): δ7.14 (s, 1H), 7.44 (s, 1H), 7.77 (s, 1H), 7.89 (s, 1H), 10.38 (s, 1H), 12.4 (br. s, 1H), ca. 15.5 (very br. s, 1H).

We claim:

1. A compound of formula I

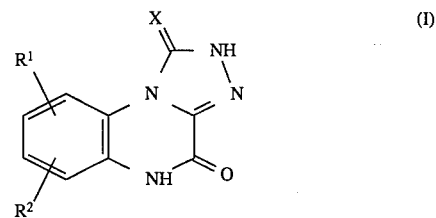

wherein one of $R^1$ and $R^2$ is a 5- or 6-membered nitrogen-containing heterocyclic ring which is optionally substituted with one, two or three substituents, wherein each substituent is independently phenyl or $C_{1-6}$-alkyl, or one of $R^1$ and $R^2$ is a fused ring system comprising a 5- or 6-membered nitrogen-containing heterocyclic ring and a benzene, pyridine, pyrimidine or pyrazine ring, wherein the fused ring system is optionally substituted with phenyl or $C_{1-6}$-alkyl; and the other of $R^1$ and $R^2$ is hydrogen, $C_{1-6}$-alkyl, $C_{1-6}$-alkoxy, halogen, $NO_2$, $NH_2$, CN, $CF_3$, $COC_{1-6}$-alkyl or $SO_2NR'R''$, wherein R' and R'' are independently hydrogen or $C_{1-6}$-alkyl; and X is O or S; or a pharmaceutically acceptable salt thereof.

2. The compound according to claim 1, wherein one of $R^1$ and $R^2$ is triazolyl which is optionally substituted.

3. The compound according to claim 1, wherein one of $R^1$ and $R^2$ is imidazolyl which is optionally substituted.

4. The compound according to claim 1, wherein one of $R^1$ and $R^2$ is piperidino which is optionally substituted.

5. The compound according to claim 1, wherein one of $R^1$ and $R^2$ is piperidyl which is optionally substituted.

6. The compound according to claim 1, wherein one of $R^1$ and $R^2$ is piperazinyl which is optionally substituted.

7. The compound according to claim 1, wherein one of $R^1$ and $R^2$ is morpholino which is optionally substituted.

8. The compound according to claim 1, wherein one of $R^1$ and $R^2$ is thiomorpholino which is optionally substituted.

9. The compound according to claim 1, wherein one of $R^1$ and $R^2$ is pyrrolidinyl which is optionally substituted.

10. The compound according to claim 1, wherein one of $R^1$ and $R^2$ is pyrazolyl which is optionally substituted.

11. The compound according to claim 1, wherein one of $R^1$ and $R^2$ is pyrazinyl which is optionally substituted.

12. The compound according to claim 1, wherein one of $R^1$ and $R^2$ is indolinyl which is optionally substituted.

13. The compound according to claim 1, wherein one of $R^1$ and $R^1$ is isoindolinyl which is optionally substituted.

14. The compound according to claim 1, wherein one of $R^1$ and $R^2$ is benzimidazolyl which is optionally substituted.

15. The compound according to claim 1, wherein one of $R^1$ and $R^2$ is isoindolyl which is optionally substituted.

16. The compound according to claim 1, wherein one of $R^1$ and $R^2$ is indolyl which is optionally substituted.

17. The compound according to claim 1, wherein one of $R^1$ and $R^2$ is indazolyl which is optionally substituted.

18. The compound according to claim 1, wherein one of $R^1$ and $R^2$ is purinyl which is optionally substituted.

19. The compound according to claim 1 which is
7-(1H-Imidazol-1-yl)[1,2,4]triazolo[4,3-a]quinoxaline-1,4(2H,5H)-dione;
7-(1H-Imidazol-1-yl)-8-trifluoromethyl[1,2,4]triazolo[4,3-a]quinoxaline-1,4(2H,5H)-dione;
8-Bromo-7-(1H-imidazol-1-yl)[1,2,4]triazolo-[4,3-a]quinoxaline-1,4(2H,5 H)-dione;
8-(2-Methyl-1H-imidazol-1-yl)-7-trifluoromethyl[1,2,4]triazolo[4,3 -a]quinoxaline-1,4(2H,5H)-dione;
8-(4-Methyl-1H-imidazol-1-yl)-7-trifluoromethyl[1,2,4]triazo- [4,3a]quinoxaline-1,4(2H,5H)-dione;
8-(1H-Imidazol-1-yl)-7-trifluoromethyl[1,2,4]triazolo[4,3-a]quinoxaline-1,4(2H,5H)-dione;
8-(2,4-Dimethyl-1H-imidazol-1-yl)-7-trifluoromethyl[1,2,4]triazolo[4,3 -a]quinoxaline-1,4(2H,5H)-dione;
8-(1H-Imidazol-1-yl)-7-nitro[1,2,4]triazolo[4,3-a]quinoxaline-1,4(2H,5 H)-dione;
8-(4-Phenyl-1H-imidazol-1-yl)-7-nitro[1,2,4]triazolo[4,3-a]quinoxaline-1,4(2H,5H)-dione;
8-(2-Isopropyl-1H-imidazol-1-yl)-7-nitro[1,2,4]triazolo[4,3-a]quinoxaline-1,4(2H,5H)-dione;
8-(2-n-Propyl-1H-imidazol-1-yl)-7-nitro[1,2,4]triazolo[4,3-a]quinoxaline-1,4(2H,5H)-dione;
8-(2-Ethyl-4-methyl-1H-imidazol-1-yl)-7-trifluoromethyl[1,2,4]triazolo[4,3 -a]quinoxaline-1,4(2H,5H)-dione;
8-(2-n-Propyl-1H-imidazol-1-yl)-7-trifluoromethyl[1,2,4]triazolo[4,3 -a]quinoxaline-1,4(2H,5H)-dione;
8-(2-Isopropyl-1H-imidazol-1-yl)-7-trifluoromethyl[1,2,4]triazolo[4,3 -a]quinoxaline-1,4(2H,5H)-dione;
8-(4-Methyl-2-phenyl-1H-imidazol-1-yl)-7-trifluoromethyl[1,2,4]triazolo-[4,3-a]quinoxaline-1,4(2H,5H)-dione;
7-Chloro-8-(2-ethyl-4-methyl-1H-imidazol-1-yl)[1,2,4]triazolo[4,3 -a]quinoxaline-1,4(2H,5H)-dione;
7-Cyano-8-(1H-imidazol-1-yl)[1,2,4]triazolo[4,3-a]quinoxaline-1,4(2H,5 H)-dione;
7-Cyano-8-(2-ethyl-4-methyl-1H-imidazol-1-yl)[1,2,4]triazolo[4,3-a]quinoxaline-1,4(2H,5H)-dione;
8-(1H-imidazol-1-yl)-1-thioxo-7-trifluoromethyl[1,2,4]triazolo[4,3-a]quinoxalin-4(5H)-one; or a pharmaceutically acceptable salt thereof.

20. The compound according to claim 1 which is
8-Morpholino-7-trifluoromethyl[1,2,4]triazolo[4,3-a]quinoxaline-1,4(2H,5 H)-dione;
8-Morpholino-7-nitro[1,2,4]triazolo[4,3-a]quinoxaline-1,4(2H,5H)-dione; or a pharmaceutically acceptable salt thereof.

21. The compound according to claim 1 which is 8-Piperidino-7 -trifluoromethyl[1,2,4]triazolo[4,3-a]quinoxaline-1,4(2H,5H)-dione; or a pharmaceutically acceptable salt thereof.

22. The compound according to claim 1 which is 8-(4-Methylpiperazin-1-yl)-7 -trifluoromethyl[1,2,4]triazolo[4,3-a]quinoxaline-1,4(2H,5H)-dione; or a pharmaceutically acceptable salt thereof.

23. The compound according to claim 1 which is 7-Nitro-8 -thiomorpholino-[1,2,4]triazolo[4,3-a]quinoxaline-1,4(2H,5H)-dione; or a pharmaceutically acceptable salt thereof.

24. The compound according to claim 1 which is 8-(1H-Benzimidazol-1-yl)-7 -nitro[1,2,4]triazolo[4,3-a]quinoxalin-1,4(2H,5H)-dione; (example 17) or a pharmaceutically acceptable salt thereof.

25. A pharmaceutical composition comprising a compound according to claim 1 and a pharmaceutically acceptable carrier or diluent.

26. The pharmaceutical composition according to claim 25 in the form of a dosage unit containing about 10–200 mg of the compound.

27. A method of treating a disorder related to hyperactivity of the excitatory neurotransmitters in a subject in need thereof, comprising administering to the subject an effective amount of a compound according to claim 1.

28. The method according to claim 27, wherein the disorder is related to cerebral ischemia.

29. The method according to claim 27, wherein the disorder is Parkinson's disease.

30. A method of treating a disorder related to hyperactivity of the excitatory neurotransmitters in a subject in need thereof, comprising administering to the subject an effective amount of a pharmaceutical composition according to claim 20.

31. The method according to claim 30, wherein the disorder is related to cerebral ischemia.

32. The method according to claim 30, wherein the disorder is Parkinson's disease.

* * * * *